US008703101B2

(12) United States Patent

Bernatchez et al.

(10) Patent No.: US 8,703,101 B2

(45) Date of Patent: Apr. 22, 2014

(54) METHODS OF DETERMINING NOX IN A WOUND SAMPLE

(75) Inventors: Stephanie F. Bernatchez, Woodbury, MN (US); Vinod P. Menon, Woodbury, MN (US); Joseph J. Stoffel, Hastings, MN (US); Joseph A. Tucker, Shoreview, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 13/388,360

(22) PCT Filed: Aug. 3, 2010

(86) PCT No.: PCT/US2010/044252

§ 371 (c)(1), (2), (4) Date: Feb. 1, 2012

(87) PCT Pub. No.: WO2011/017325

PCT Pub. Date: Feb. 10, 2011

(65) Prior Publication Data

US 2012/0135444 A1 May 31, 2012

Related U.S. Application Data

(60) Provisional application No. 61/231,236, filed on Aug. 4, 2009.

(51) Int. Cl.

*A61K 49/00* (2006.01)

(52) U.S. Cl.

USPC .............................................. 424/9.1; 435/23

(58) Field of Classification Search

None

See application file for complete search history.

(56) References Cited

U.S. PATENT DOCUMENTS

| | | | | |
|---|---|---|---|---|
| 4,003,706 | A | 1/1977 | Szekely | |
| 5,065,768 | A | 11/1991 | Coleman et al. | |
| 5,100,620 | A | 3/1992 | Brenneman | |
| 5,976,895 | A | 11/1999 | Cipkowski | |
| 6,332,871 | B1 | 12/2001 | Douglas et al. | |
| 7,458,942 | B2 | 12/2008 | Bohannon et al. | |
| 2002/0188263 | A1 | 12/2002 | Le Bui et al. | |
| 2003/0134332 | A1 | 7/2003 | Boykin, Jr. | |
| 2003/0157728 | A1* | 8/2003 | Uhl et al. | 436/177 |
| 2004/0193030 | A1 | 9/2004 | Aston et al. | |
| 2006/0069359 | A1 | 3/2006 | DiPalma et al. | |
| 2006/0172000 | A1 | 8/2006 | Cullen et al. | |

FOREIGN PATENT DOCUMENTS

| | | |
|---|---|---|
| GB | 2 323 166 | 9/1998 |
| JP | 2006-337252 | 12/2006 |
| WO | WO 2008/119974 | 10/2008 |
| WO | WO 2011/017317 | 2/2011 |

OTHER PUBLICATIONS

Yager et al. "Wound Fluids: A Window into the Wound Environment?" (2007) Lower Extremity Wounds, vol. 6: 262-272.*

Muscara et al. "Wound collagen deposition in rats: effects of an NO-NSAID and a selective COX-2 inhibitor." (2000) British Journal of Pharmacology, vol. 129: 681-686.*

Schaffer et al. "Diabetes-impaired healing and reduced wound nitric oxide synthesis: A possible pathophysiologic correlation." (1997) Surgery, vol. 121: 513-519.*

Viral Immunology Center Recommended Sample Collection, Storage & Shipment (1999) Georgia State University, 1-17.*

Shorrock, "The exploration of Tissue pH in wounds and its relationship to bacterial contamination." (2000) Worcester Polytechnic Institute 1-131.*

Boykin, J.V.; "Ischemic Vascular Disease, Nitric Oxide Deficiency, and Impaired Wound Healing"; Vascular Disease Management; vol. 3; 2006; pp. 2A-11A.

Boykin, J.V. et al., "Treatment of Elevated Homocysteine to Restore Normal Wound Healing: A Possible Relationship Between Homocysteine, Nitric Oxide, and Wound Repair", Advances in Skin & Wound Care, vol. 18, No. 6, 2005; pp. 297-298 and 300.

Braman, R.S. et al.; "Nanogram Nitrite and Nitrate Determination in Environmental and Biological Materials by Vanadium (III) Reduction with Chemiluminescence Detection"; Anal. Chem.; vol. 61, No. 24; 1989; pp. 2715-2718.

Bryan,N.S. et al.; "Methods to detect nitric oxide and its metabolites in biological samples", Free Radical Biology & Medicine, vol. 43; 2007; pp. 645-657.

doRosário, M. et al., "Nitric oxide and human thermal injury short term outcome"; Burns, vol. 24, 1998; pp. 207-212. (XP-002601231).

Everett, S.A. et al.; "Nitric oxide in biological fluids: analysis of nitrite and nitrate by high-performance ion chromatography"; Journal of Chromatography A, vol. 706, 1995; pp. 437-442.

Friedberg,M.A. et al.; "Analysis of nitrate in biological fluids by capillary electrophoresis," Journal of Chromatography A, vol. 781, 1997; pp. 491-496.

Gamelli, R. et al.; "Burn-Induced Nitric Oxide Release in Humans", The Journal of Trauma, Injury, Infection, and Critical Care; vol. 39, No. 5; 1995; pp. 869-878.

Inoue, H. et al.; "Determination of nitrotyrosine and related compounds in biological specimens by competitive enzyme immunoassay", Nitric Oxide, vol. 7; 2002; pp. 11-17. (XP-002601233).

Kelm, M. et al.; "Serum nitrite sensitively reflects endothelial NO formation in human forearm vasculature: evidence for biochemical assessment of endothelial L-arginine-NO pathway"; Cardiovascular Research, vol. 41, 1999; pp. 765-772.

Marzinzig, M. et al.; "Improved Methods to Measure End Products of Nitric Oxide in Biological Fluids; Nitrite, Nitrate, and S-Nitrosothiols"; Nitric Oxide: Biology and Chemistry; vol. 1, No. 2; 1997; pp. 177-189.

Misko, T.P. et al.; "A Fluorometric Assay for the Measurement of Nitrite in Biological Samples", Analytical Biochemistry; vol. 214; 1993; pp. 11-16.

Monaghan, J.M. et al.; "Determination of nitrite and nitrate in human serum", Journal of Chromatography A; vol. 770; 1997; pp. 143-149.

(Continued)

*Primary Examiner* — Jon P Weber

*Assistant Examiner* — Teresa E Knight

(57) ABSTRACT

The present disclosure provides devices and rapid methods to acquire a wound sample to detect and measure NOx, and optionally, one or more other analytes that are indicative of the status of a wound.

18 Claims, 2 Drawing Sheets

(56) References Cited

OTHER PUBLICATIONS

Sonoda, M. et al.; "An Assay Method for Nitric Oxide-Related Compounds in Whole Blood"; Analytical Biochemistry; vol. 247; 1997; pp. 417-427.

Tsikas, D,; "Simultaneous Derivatization and Quantification of the Nitric Oxide Metabolites Nitrite and Nitrate in Biological Fluids by Gas Chromatography/Mass Spectrometry", Analytical Chemistry, vol. 72, No. 17; 2000; pp. 4064-4072.

* cited by examiner

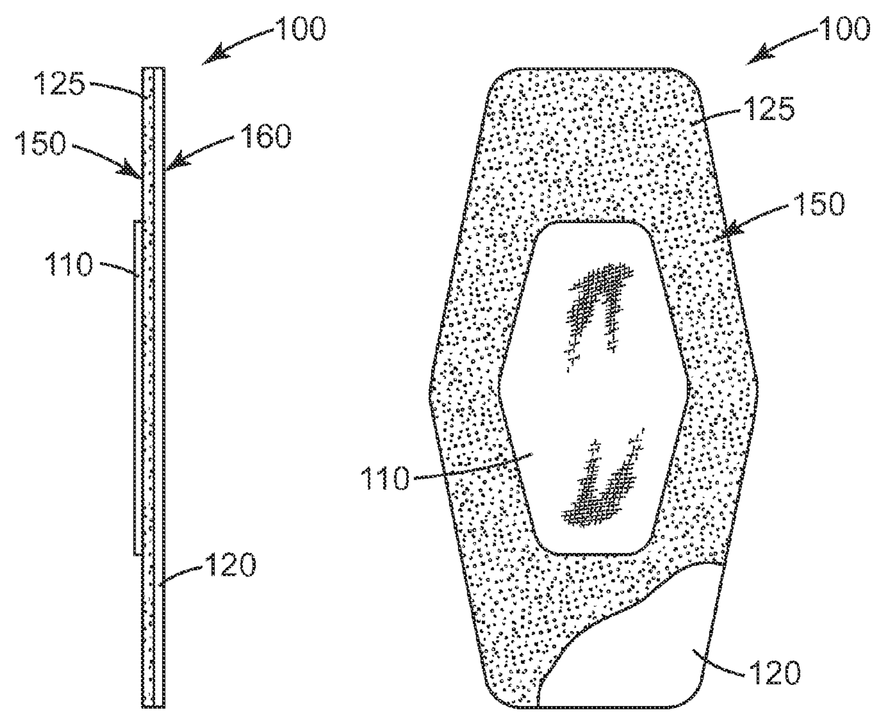
Fig. 1a
Fig. 1b
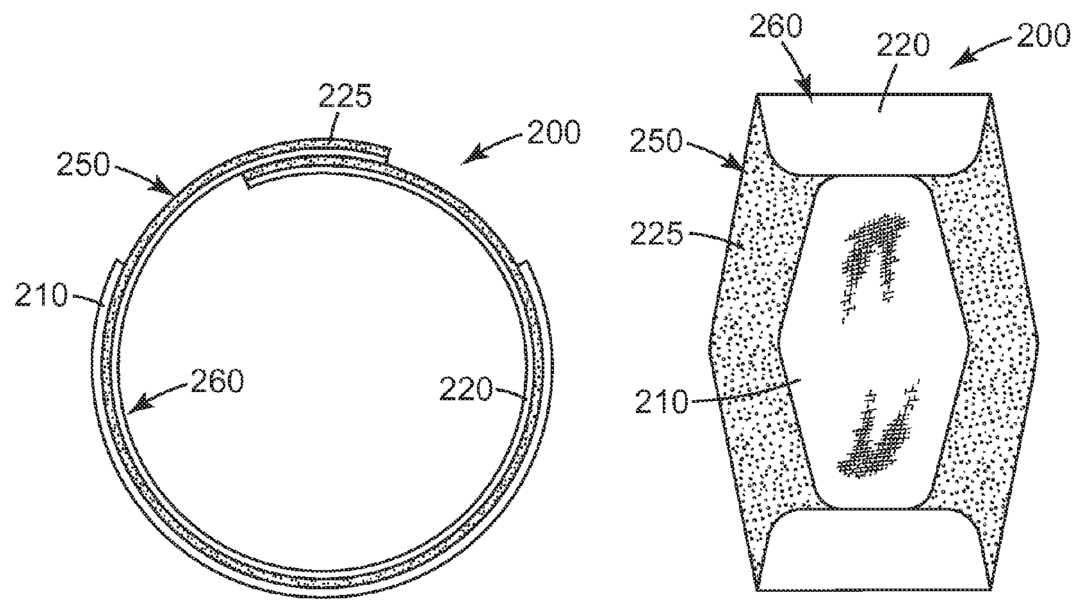
Fig. 2a
Fig. 2b

METHODS OF DETERMINING NOX IN A WOUND SAMPLE

CROSS REFERENCE TO RELATED APPLICATIONS

This application claims priority to U.S. Provisional Patent Application No. 61/231,236, filed Aug. 4, 2009, which is incorporated herein by reference.

BACKGROUND

In mammals, injury triggers a complex cascade of cellular and biochemical events that result in a healed wound. Wound healing is a complex dynamic process that results in the restoration of anatomic continuity and function; an ideally healed wound is one in which the wounded tissue has returned to normal anatomic structure, function and appearance.

Certain factors, such as poor circulation and/or microbial contamination can delay or prevent the normal processes associated with wound healing. Early diagnosis of abnormal wound healing can permit a clinician to intervene with appropriate treatments (e.g., antibiotic therapy).

The status of a wound can be assessed by determining the presence and/or amount of certain analytes at the wound site. The analytes may be soluble analytes (e.g., total protein; enzymes, such as matrix metalloproteinase, plasmin, elastase, lactate dehydrogenase; and oxides of nitrogen, such as nitric oxide). The analytes may be certain types of cells (e.g., neutrophils, macrophages, fibroblasts).

Assessing a wound site typically involves the collection of sample material. Swabs are the most commonly-used device for collecting samples, but their efficacy is limited for certain analytical tests. Biopsies are used in certain situations, but they are invasive and can cause additional trauma to the wound site, further delaying the healing process. There is a need for a simple, noninvasive wound sampling method that is compatible with a plurality of analytical tests.

SUMMARY

Evidence of endothelial dysfunction refers to, among other things, abnormally low nitric oxide (NO) production by vascular endothelial tissue. Detecting the presence/amount of NO-related compounds in tissue (e.g., a wound site) can be useful in predicting the future clinical outcome for existing medical conditions. Known methods for detecting nitric oxide in a wound include contacting "nitrate-free" absorbent paper to a wound for 24 hours, followed by measuring the level of NO in the filter paper.

Using a rapid, sensitive method of nitrate detection, the inventors have surprisingly found that "nitrate free" filter paper comprises sufficient reactive nitrate to interfere with the detection of NO-related compounds. Using the same nitrate detection method, the inventors have discovered sample acquisition devices that that do not comprise levels of reactive nitrate that could substantially interfere with the detection of physiological amounts of NO-related compounds in wound fluid. Furthermore, these sample acquisition devices are sufficiently absorbent to rapidly collect a sample of wound fluid. The inventive methods provide for rapid detection of clinically-relevant amounts of NO-related compounds in a wound.

Thus, in one aspect, the present disclosure provides a method of determining the state of a wound. The method can comprise providing a sample acquisition device that is substantially free of reactive nitrates, contacting the sample acquisition device with a wound site for a period of time sufficient to collect wound exudate, extracting a portion of the exudate from the dressing, and detecting endogenous $NO_x$ in the extracted portion.

In another aspect, the present disclosure provides a method of determining the state of a wound. The method can comprise providing at least two sample acquisition devices that are substantially free of reactive nitrates, contacting a first sample acquisition device with a wound site for a period of time sufficient to collect wound exudate, cleansing the wound site, contacting a second sample acquisition device with the wound site for a period of time sufficient to collect wound exudate, extracting a portion of the exudate from each sample acquisition device, and detecting endogenous $NO_x$ in the extracted portion from each sample acquisition device.

In any of the above embodiments, the method can further comprise detecting in the extracted portion at least one analyte in addition to endogenous $NO_x$. In any of the above embodiments, detecting endogenous $NO_x$ can comprise detecting $NO_x$ by spectrometry. In any of the above embodiments, detecting endogenous $NO_x$ can comprise detecting $NO_x$ by colorimetry or fluorometry. In any of the above embodiments, detecting in the extracted portion at least one analyte in addition to endogenous $NO_x$ can comprise detecting total protein.

In any of the above embodiments, detecting total protein can comprises detecting protein colorimetrically. In any of the above embodiments, detecting protein colorimetrically can comprise conducting a BCA assay, a Lowry protein assay, a Biuret assay, or a Bradford protein assay.

In any of the above embodiments, detecting in the extracted portion at least one analyte in addition to endogenous $NO_x$ can comprise detecting a protease. In any one of the above embodiments, detecting a protease can comprise detecting a matrix metalloproteinase. In any of the above embodiments, detecting a matrix metalloproteinase can comprise detecting a matrix metalloproteinase fluorometrically. In some embodiments, the matrix metalloproteinase can comprise MMP-9.

In any of the above embodiments, detecting in the extracted portion at least one analyte in addition to endogenous $NO_x$ can comprises detecting total protein, a protein or a fragment thereof, a protease, a polynucleotide, a cytokine, a growth factor, a microorganism or an analyte therefrom, or a combination of any two or more of the foregoing. In any of the above embodiments, extracting the exudate comprises centrifuging the sample acquisition device.

In any of the above embodiments, the method further can comprise the step of measuring the pH of the wound. In any of the above embodiments, the method further can comprise cleansing the wound. In any of the above embodiments, prior contacting the sample acquisition device with the wound site, a wound dressing can be removed from the wound site. In any of the above embodiments, contacting the sample acquisition device with a wound site for a period of time can comprise manually pressing the sample acquisition device against the wound site.

DEFINITIONS

"$NO_x$", as used herein, refers to nitric oxide-related (NO-related) compounds. NO-related compounds include nitric oxide and derivatives thereof. NO derivatives include nitrate compounds and nitrite compounds.

The use of "including," "comprising," or "having" and variations thereof herein is meant to encompass the items listed thereafter and equivalents thereof as well as additional items. Unless specified or limited otherwise, the term "coupled", "attached", "connected" and variations thereof is used broadly and encompasses both direct and indirect couplings. Further, the term "coupled" is not restricted to physical or mechanical couplings. It is to be understood that other embodiments may be utilized, and structural or logical changes may be made without departing from the scope of the present disclosure. Furthermore, terms such as "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, an article that comprises "a" sample-collecting region can be interpreted to mean that the article includes "one or more" sample-collecting regions. Similarly, a method for detecting "an" analyte can be interpreted to mean that the method can involve detecting "one or more" analyte.

The term "and/or" means one or all of the listed elements or a combination of any two or more of the listed elements.

As used herein, the term "or" is generally employed in its sense including "and/or" unless the content clearly dictates otherwise.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The present invention will be further explained with reference to the drawing figures listed below, where like structure is referenced by like numerals throughout the several views.

FIG. 1*a* is a side view of one embodiment of a sample acquisition device according to the present disclosure FIG. 1*b* is a top view, partially in section of the sample acquisition device of FIG. 1*a*.

FIG. 2*a* is a side view of the sample acquisition device of FIG. 1*a* in one configuration for obtaining a sample.

FIG. 2*b* is a top view of the sample acquisition device of FIG. 1*a* in an alternative configuration for obtaining a sample.

DETAILED DESCRIPTION

Figure 3A:
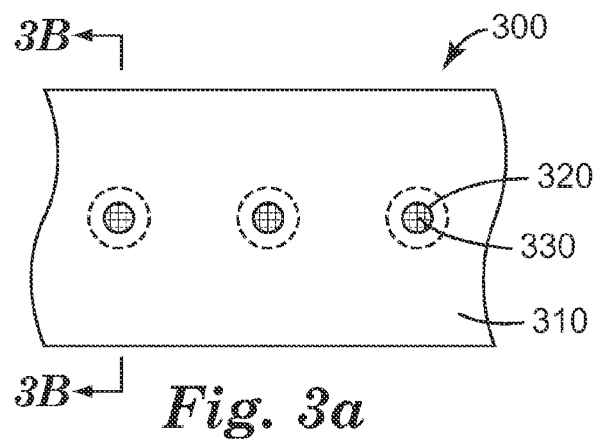
FIG. 3*a* is a top view of one embodiment of a device for detecting nitrate in a sample.

The present disclosure generally relates to articles and methods for assessing the status of a wound. The inventive articles and methods provide a rapid test to measure physiological levels of $NO_x$ and, optionally, other analytes found in wound exudate. Physiological levels of NOx in wound fluid can be as low as approximately 1 mM (J. V. Boykin, "Ischemic Vascular Disease, Nitric Oxide Deficiency, and Impaired Wound Healing", Vascular Disease Management, 2006, vol. 3, pp. 2A-11A)

The inventors have surprisingly discovered that commercially-available "nitrate-free" sample collection materials may contain sufficient reactive nitrate to interfere with a rapid method for measuring physiological levels of $NO_x$.

The articles permit rapid collection of a sample of biological fluid (e.g., from a wound) and advantageously are constructed from materials that are substantially free of reactive nitrates that may interfere with the detection of physiological levels of $NO_x$. A sample acquisition device that is "substantially free of reactive nitrates", as used herein, is an article that releases less than or equal to about 1 μM reactive nitrate compounds into a nitrate-free liquid sample that is first absorbed by and, subsequently, released from the sample acquisition device. Furthermore, the articles are constructed from materials that do not substantially interfere with the detection of physiological levels of other analytes (e.g., total protein, metalloproteinases) that may be indicative of the status of a wound. The inventive methods advantageously can provide accurate, qualitative or quantitative measurements of analytes that are indicative of the healing status of a wound site.

Wound Analytes:

The devices and methods of the present disclosure are useful to collect material (e.g., wound exudate) to determine the status of a wound with respect to healing and/or infection. The wound status can be determined by detecting one or more analytes that can be found in wound exudate. "Wound analyte" is used in the broadest sense to include biomolecules that can be found in and/or proximate a wound site and that may be indicative of the status of a wound.

"Biomolecules" can be any chemical compound that naturally occurs in living organisms, as well as derivatives or fragments of such naturally occurring compounds. Biomolecules consist primarily of carbon and hydrogen, along with nitrogen, oxygen, phosphorus, and sulfur. Other elements sometimes are incorporated but are much less common. Biomolecules include, but are not limited to, proteins, antibodies, polypeptides, carbohydrates, polysaccharides, lipids, fatty acids, steroids, prostaglandins, prostacyclines, vitamins, cofactors, cytokines, and nucleic acids (including DNA, RNA, nucleosides, nucleotides, purines, and pyrimidines), metabolic products that are produced by living organisms including, for example, antibiotics and toxins. Thus, as used herein, the term "biomolecule" includes, but is not limited to, both unmodified and modified molecules (e.g., glycosylated proteins) and fragments thereof (e.g., protein fragments). Fragments of biomolecules can include those resulting from hydrolysis due to enzymatic (e.g., proteolytic) processes, for example.

The exudate can be tested for the presence or amount of an oxide of nitrogen (e.g., nitric oxide), for example, that is present in the wound (i.e., endogenous to the wound). In some embodiments, the exudate can further be tested for certain biomolecules that are known to be associated with wounds, infected wounds, and/or wound healing.

Certain biomolecules are known in the art to be associated with an inflammatory response. Nonlimiting examples of said biomolecules that can be found in wound fluid include a fibronectin fragment, a neutrophil protease or a macrophage protease. An elevated level of these biomolecules may correlate with increased likelihood of clinical infection. Other biomolecules that are found in wound fluid and can be used to indicate the status of a wound include, but are not limited to, elastase, MMP-9, MMP-8, MMP-1, MMP-12, cathepsin G, collagen propeptide, a collagen telopeptide, a protease inhibitor, plasmin, lactate dehydrogenase, a cathepsin, a cytokine, a peroxidase enzyme, a cortisol free radical, a growth factor, a protease enzyme, neutrophil elastase, plasmin, low molecular weight gelatinases and latent or active elastases, interleukin converting enzymes or tumor necrosis factor (TNFα) converting enzymes. Other biomolecules that can be indicators of the status of a wound include interleukins such as IL-1β, IL-4, IL-6, IL-8, IL-10, IL-18, MCP-1, MCP-2, MCP-3 (monocyte chemoattractant proteins), MIP-1α, MIP-Iβ, MIP-2 (macrophage inflammatory proteins); interferons IFN-alpha, IFN-beta, and IFN-gamma; GM-CSF (granulocyte/macrophage colony stimulating factor); PF-4 (Platelet factor 4); and RANTES (CCL5). Other biomolecules in a wound exudate that may indicate the status of the wound include proteins and/or polynucleotides (e.g., ribonucleic acid, deoxyribonucleic acid).

Devices for Collecting Wound Exudate:

The present disclosure provides devices for acquiring a sample of exudate from a wound. Boykin et al. (Advances in Skin & Wound Care, 2005, vol. 18, pp. 297-300; which is incorporated herein by reference in its entirety) describe a method of detecting $NO_x$ in a wound, wherein a "nitrate-free" filter paper is applied to a wound for approximately 24 hours and, subsequently, the amount of $NO_x$ in the wound fluid collected by the filter paper is analyzed. The inventors have surprisingly found that, if "nitrate-free" filter paper similar to that used by Boykin et al. is used in a rapid method (i.e., the filter paper is contacted with a wound site for a period of less than 24 hours), there is a sufficient amount of reactive nitrate in the "nitrate-free" filter paper to interfere with the measurement of physiological levels of $NO_x$.

Without being bound by theory, the inventors propose that, when "nitrate-free" filter paper contacts a wound for an extended period of time, reactive nitrates in the filter paper can be diluted by the wound exudate (possibly, by diffusing out of the paper), thereby permitting the measurement of relatively low levels of $NO_x$ in the wound fluid. According to the theory, placing the filter paper in contact with a wound for a relatively short period of time may not allow enough of the reactive nitrate to diffuse out of the filter paper and, thereby, the residual reactive nitrate in the filter paper may interfere with the detection of low levels of endogenous $NO_x$ from the wound.

Sample acquisition devices of the present disclosure are substantially free of reactive nitrates and nitrites, which can interfere with the measurements of endogenous $NO_x$ in a wound. Thus, the sample can be collected rapidly and the $NO_x$ can be measured without interference from the sample acquisition device. Furthermore, the devices are designed and constructed such that they do not substantially interfere with a plurality of other test procedures for analytes that are known in the art to indicate the status of a wound. Interference may be caused by the release of interfering chemicals and/or polymers from the device into the wound exudate. In particular, in some embodiments, the devices are substantially free of materials (e.g., monomers, nylon polymers) that may interfere with a test procedure (e.g., the BCA assay) for total protein. In some embodiments, the devices are substantially free of materials (e.g., cellulosics), which may contain relatively high and/or highly variable amounts of nitrates or nitrites. In certain preferred embodiments, the devices are substantially free of materials that can interfere with either a test procedure for total protein or a test procedure for $NO_x$.

Devices for collecting a sample of exudate releasably acquire (e.g., by adsorption and/or absorption) an amount of wound exudate sufficient to perform one or more test procedures. In some embodiments, the device will releasably acquire at least about 10 microliters of exudate. In some embodiments, the device will releasably acquire at least about 50 microliters of wound exudate. In some embodiments, the device will releasably acquire at least about 100 microliters of wound exudate. In some embodiments, the device will releasably acquire at least about 200 microliters of wound exudate.

In some methods of use, it may be desirable to collect a sample of wound exudate and store it in the sample acquisition device for a period of time. Therefore, in some embodiments, it may be desirable to use a sample-collection device that is stable (e.g., maintains its structural and/or chemical stability) at the conditions (e.g., time, temperature, humidity, etc.) in which the device will be stored.

In some methods of use, it may be desirable to process the wound exudate in the sample-collection device before the wound exudate is removed from the sample acquisition device. For example, it may be desirable to freeze a device containing a sample, in order to preserve the sample for subsequent testing. Therefore, in some embodiments, it may be desirable to use a sample acquisition device that is stable to the process (e.g., freezing).

An example of a suitable sample acquisition device is a NEXCARE Soft 'n Flex first aid dressing (catalog no. 672-35), available from 3M Company (St. Paul, Minn.). The 3M NEXCARE "Soft 'n Flex" First Aid Dressing (FAD) absorbent pad is a polyethylene/polyester/EVA polymer with a surfactant treatment and $TiO_2$. The pads are STRATEX material from DelStar Technologies Inc., of Middletown, Del. The NEXCARE first aid dressing can collect up to several hundred microliters of wound exudate, can be processed (e.g., by freezing) and, as shown herein, does not substantially interfere with a plurality of tests for analytes that are endogenous to a wound site.

FIG. 1 a. shows a side view of one embodiment of a sample acquisition device 100 according to the present disclosure. The device 100 comprises an absorbent pad 110, which may be coupled to an optional backing 120. The backing 120 may further comprise an adhesive layer 125, which can function to couple the absorbent pad 110 to the backing 120.

The absorbent pad 110 comprises at least one absorbent material capable of adsorbing and/or absorbing wound exudate comprising fluid. The absorbent material can be a fibrous material (e.g., polymeric fibers) or a foam material (e.g., an open-cell foam or a closed-cell foam). The absorbent material is substantially free of components that may interfere with a test procedure to detect $NO_x$ in a wound exudate. Preferably, the absorbent material is substantially free of components that may interfere with a test procedure to detect other analytes (e.g., total protein) in a wound. An example of a preferred absorbent fiber is a polyester fiber (e.g., DACRON polyester fibers). In some embodiments, the polyester fibers may comprise a coating (e.g., a hydrophilic coating). In some embodiments, the absorbent pad 110 may further comprise an outer layer (not shown). The outer layer can function to facilitate the movement of wound exudate from the wound site to the absorbent material and/or to retain the absorbent material.

The backing 120 may be constructed from a number of suitable materials including, for example, metal (e.g., a metal foil), glass, a film (e.g., a plastic film), and combinations thereof. In some embodiments, the backing 120 is substantially water-resistant. In some embodiments, the backing 120 may comprise pores and/or perforations (not shown), which permit the passage of gas (e.g., air) and/or liquids through the backing. In certain embodiments, it may be desirable to decontaminate, disinfect, or sterilize the device 100 before use. In these embodiments, the materials for the absorbent pad 110 and/or the backing 120 can be selected for their compatibility with the decontamination, disinfection, or sterilization process.

FIG. 1*a* shows that the device 100 comprises two major surfaces: first major surface 150 and second major surface 160, respectively. In this embodiment, the first major surface 150 includes the absorbent pad 120 and, thus, it is the side of the device 100 that can be oriented toward a wound site (not shown) to allow direct contact between the absorbent pad 110 and the wound. In some embodiments (e.g., in an embodiment where the backing 120 comprises perforations (not shown)), the second major surface 160 of the sample acquisition device 100 can be contacted with the wound site and the wound exudate can pass through the perforations and onto and/or into the absorbent pad.

FIG. 1*b* shows a top perspective view, partially in section, of the sample acquisition device 100 of FIG. 1*a*. It can be seen that the backing 120 extends outside the perimeter of the absorbent pad 110. In use, when the absorbent pad 110 is contacted with a wound site, the adhesive layer 125 can be contacted with the area (e.g., skin) surrounding the wound site and the adhesive layer 125 can hold the sample acquisition device securely in place while the wound exudate is collected from the wound site.

FIG. 2*a* shows a side view of the sample acquisition device 100 of FIG. 1 configured to obtain a wound sample. The device is folded back on itself such that the adhesive layer 225 on the first major surface 250 of the device 200 contacts the backing 220 on the second major surface 260 of the device. This configuration of device 200 conveniently forms a loop that can be grasped by the operator to hold the device 200 while the absorbent pad 210 is contacted with a wound site.

FIG. 2*b* shows a top view of an alternative configuration of device for obtaining a wound sample. In this embodiment, a portion of backing 220 is folded toward the absorbent pad 210 such that the adhesive layer 225 sticks to itself. In this configuration, an operator can grasp the backing 260 where it is folded over the adhesive layer 225 while contacting the absorbent pad 210 of the first major surface 250 to a wound. In this configuration, sufficient adhesive layer 225 may be available to secure the device 200 to a wound site for a period of time.

It will be recognized by a person of ordinary skill in the art that the absorbent pad disclosed herein can be coupled to a number of structures (e.g., a handle, a shaft, forceps, or the like) other than the backings described herein. In some embodiments, the absorbent pad can be used without a backing, for example, to collected exudate from a wound site.

Method of Collecting and Analyzing a Wound Exudate:

The present disclosure provides a method for detecting one or more analytes in a wound. The wound may be a result of trauma (e.g., a puncture wound), a medical condition (e.g., a pressure ulcer or an abscess), or a surgical wound (e.g., an incision), to skin tissue or a mucous membrane. The method includes collecting a sample of exudate from the wound site.

In some embodiments, the wound is analyzed before or after the sample of the exudate is obtained. For example, the pH of the wound can be analyzed by methods that are known in the art.

Methods of the present disclosure include the collection of wound exudate using a sample acquisition device. In some embodiments, the exudate is collected by contacting the absorbent pad of a sample acquisition device directly against the wound site. In some embodiments, prior contacting the absorbent pad to the wound site, a dressing is removed from the wound. In some embodiments, the exudate is collected by contacting the absorbent pad indirectly with the wound site (e.g., the sample acquisition device is contacted with a drainage tube, a wound fluid collection container (e.g., a negative-pressure wound therapy device), or a wound dressing saturated with wound exudate).

During contact with the wound site, at least a portion of the exudate fluid, which may contain some cells and/or fragments of cells, is transferred to the absorbent pad of the sample acquisition device. At least a portion of the exudate is retained (e.g., by absorption and/or adsorption) on and/or in the absorbent pad after the sample acquisition device is removed from contact with the wound site.

The absorbent pad of the sample acquisition device is contacted with the wound for a period of time sufficient to collect a sample of exudate. In some embodiments, the absorbent pad of the dressing is contacted with the wound for about 24 hours or less. In some embodiments, the absorbent pad is contacted with the wound for about 30 minutes or less. In some embodiments, the absorbent pad is contacted with the wound for about 10 minutes or less. In some embodiments, the absorbent pad is contacted with the wound for about 5 minutes or less. In some embodiments, the absorbent pad is contacted with the wound for 1 minute or less. In some embodiments, the absorbent pad is contacted with the wound for about 30 seconds or less. In some embodiments, the absorbent pad is contacted with the wound for 10 seconds or less.

Typically, the absorbent pad of the sample acquisition device is contacted with the wound site using manual pressure against the opposite side of the absorbent pad. The dressing is held in contact with the wound site until a sufficient amount of exudate is collected on and/or in the absorbent pad and the sample acquisition device is subsequently removed from contact with the wound. In some embodiments, the adhesive backing of the sample acquisition device can be folded back on itself, as shown in FIG. 2*a*, forming a convenient handle for a person to grasp the sample acquisition device while contacting it with the wound site.

In an alternative embodiment (not shown), the absorbent pad of the first aid dressing is contacted with the wound while the adhesive backing is contacted with a surface (e.g., skin) adjacent the wound site. Advantageously, the adhesive backing holds the dressing in place for a period of time sufficient to collect a sample of wound exudate.

In any of the above embodiments, the absorbent pad may be repositioned one or more times at the wound site to collect additional wound exudate. The amount of wound exudate sufficient for analysis can depend on the test procedures used in the analysis. Typically, each analytical test may require about 10 microliters to about 100 hundred microliters of wound exudate.

In any of the above embodiments, the method further comprises cleansing and/or irrigating the wound site, for example, with sterile water or a sterile solution comprising saline. The wound site can be cleansed before obtaining a sample with a sample acquisition device. The wound site can be cleansed after obtaining a sample with a sample acquisition device. The wound site can be cleansed before and after obtaining a sample with a sample acquisition device. A sample can be obtained with a sample acquisition device before and after cleansing a wound site.

In some embodiments, a first sample is obtained from a wound site with a first sample acquisition device described herein, the wound is cleansed, a second sample is obtained with a second sample acquisition device described herein, the samples are extracted from the first and second sample acquisition devices, and the wound exudate from the sample acquisition devices is analyzed to detect $NO_x$ and, optionally at least one other analyte that is indicative of the status of the wound.

In any of the above embodiments, the method further can comprise processing the sample acquisition device. Processing the sample acquisition device includes, for example, processing the device for preserving, storing and/or transporting a sample of wound exudate. Non-limiting examples of processing a sample acquisition device include adding a reagent to the sample acquisition device and freezing (e.g., at −80° C.) a sample-laden sample acquisition device.

The method further comprises extracting a portion of the exudate from the sample acquisition device. Extracting is used in the broadest sense of recovering at least a portion of the wound material from the sample acquisition device. In some embodiments, the wound material can be extracted by physical means (e.g., using pressure to express fluid from the sample acquisition device, using centrifugal force to separate wound exudate from the sample acquisition device, using an electromagnetic field to separate a portion of the wound exudate from the sample acquisition device), by chemical means (i.e., using a solvent, such as water or a buffer, for example, to extract the wound material from the sample acquisition device), or a combination of physical and chemical means to extract a portion of the exudate.

In certain preferred embodiments, the sample acquisition device is selected to provide highly-efficient extraction of the wound exudate. In some embodiments, the sample acquisition device may provide for extraction and recovery of at least 50% of the wound exudate. In some embodiments, the sample acquisition device may provide for extraction and recovery of at least 60% of the wound exudate. In some embodiments, the sample acquisition device may provide for extraction and recovery of at least 70% of the wound exudate. In some embodiments, the sample acquisition device may provide for extraction and recovery of at least 80% of the wound exudate. In some embodiments, the sample acquisition device may provide for extraction and recovery of at least 90% of the wound exudate. In some embodiments, the sample acquisition device may provide for extraction and recovery of at least 95% of the wound exudate.

The method further comprises detecting endogenous $NO_x$ in the exudate. The $NO_x$ can be detected by methods that are known in the art, including those described herein. Optionally, the method further comprises detecting one or more analytes other than $NO_x$.

Detection Methods:

Methods of the present disclosure include detecting $NO_x$ in a wound exudate sample. NO is normally metabolized to certain stable products such as nitrate and nitrite, which may be assayed in urine, plasma, tissue, wound fluid, or other specimens from a patient. The level of nitrate. nitrite. or other NO-related products in a specimen serves as an indicator of the level of NO synthesis in a patient. $NO_x$ can be detected in a patient sample by methods that are known in the art, including, for example, spectrometry methods (e.g., colorimetric methods, fluorometric methods, and GC/mass spectrometry).

Methods of detecting $NO_x$ can be found, for example, in U.S. Patent Application Publication No. US 2003/0134332 and in an article by D. Tsikas ("Simultaneous Derivatization and Quantification of the Nitric Oxide Metabolites Nitrite and Nitrate in Biological Fluids by Gas Chromatography/Mass Spectrometry", *Anal. Chem.*, 2000, 72:4064-4072), each of which is incorporated herein by reference in its entirety. The level of nitrate or nitrite in the specimen can be quantified by any method known in the art which provides adequate sensitivity and reproducibility.

For example, the Griess reaction is a spectrophotometric assay for nitrate which can provide sensitive determination of nitrate and nitrite in biological fluid samples (M Marzinzig et al., Nitric Oxide 1,177 (1997), which is incorporated herein by reference in its entirety). If the Griess reaction or another nitrite assay is performed both with and without reduction of nitrate to nitrite, then nitrate values can be obtained as the difference between the nitrite values obtained for the reduced sample and the non-reduced sample. The Griess assay can be made more sensitive if a fluorescent product is obtained, e.g., by reacting nitrite with 2,3-diaminonaphalene (T P Misko et al., Anal. Biochem. 214, 11 (1993), which is incorporated herein by reference in its entirety).

Highly sensitive assays are also available which first reduce nitrite and nitrate (R S Braman and S A Hendrix, Anal. Chem. 61, 2715 (1989)) or any NO-related compound (M Sonoda et al., Anal. Biochem. 247, 417 (1997)) to NO for detection with specific chemiluminescence reagents. A variety of protocols have also been described for detecting and quantifying nitrite and nitrate levels in biological fluids by ion chromatography (e.g., S A Everett et al., J. Chromatogr. 706, 437 (1995); J M Monaghan et al., J. Chromatogr. 770, 143 (1997)), high-performance liquid chromatography (e.g., M Kelm et al., Cardiovasc. Res. 41, 765 (1999)), and capillary electrophoresis (M A Friedberg et al., J. Chromatogr. 781, 491 (1997); each of which is incorporated herein by reference in its entirety).

The "level" of NO-related product or oxidant stress-related product usually refers to the concentration (in moles per liter, micromoles per liter, or other suitable units) of the respective product in the specimen, or in the fluid portion of the specimen. However, other units of measure can also be used to express the level of the products. For example, an absolute amount (in micrograms, milligrams, nanomoles, micromoles, moles, or other suitable units) can be used, particularly if the amount refers back to a constant amount, mass, or volume of patient specimen (e.g., grams, kilograms, milliliters, liters, or other suitable units). A number of commercially available kits can be used. For example, Cayman Chemical Company (Ann Arbor, Mich.) provides kits to detect nitric oxide metabolites colorimetrically or fluorometrically.

In some embodiments, $NO_x$ in a sample can be detected by the methods described in Example 7 herein and in U.S. Patent Application No. 61/231,257, filed Aug. 4, 2009 and entitled "Method of Detecting Oxides of Nitrogen", which is incorporated herein by reference in its entirety. In one aspect, the method comprises detecting $NO_x$ in a sample by a reaction that forms a red cationic dye (Compound I), shown below:

Compound I

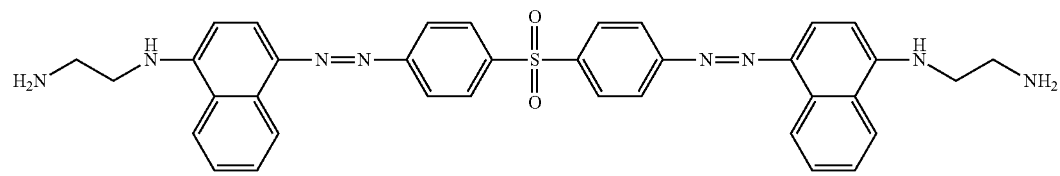

In one embodiment, the method comprises forming a mixture comprising a sample suspected of containing $NO_x$ and N-(1-naphthyl)-ethylenediamine. In one embodiment, the method of detecting $NO_x$ comprises forming a mixture including a sample suspected of containing $NO_x$ and 4,4'-sulfonyldianiline. In one embodiment, the method of detecting $NO_x$ comprises forming a mixture including sample suspected of containing $NO_x$, $VCl_3$, and HCl. In one embodiment, the method of detecting $NO_x$ comprises forming a mixture including a sample suspected of containing $NO_x$, $VCl_3$, HCl, and 4,4'-sulfonyldianiline. In one embodiment, the method of detecting $NO_x$ comprises forming a mixture including a sample suspected of containing $NO_x$, N-(1-naphthyl)-ethylenediamine, and 4,4'-sulfonyldianiline. In one embodiment, the method of detecting $NO_x$ comprises forming a mixture including a sample suspected of containing $NO_x$, $VCl_3$, HCl, and N-(1-naphthyl)-ethylenediamine.

In one embodiment, the method of detecting $NO_x$ comprises forming a mixture including a sample suspected of containing $NO_x$, $VCl_3$, HCl, 4,4'-sulfonyldianiline, and N-(1-naphthyl)-ethylenediamine. Without being bound by theory, Reaction Scheme I shows a proposed pathway for the formation of a red cationic dye to detect $NO_3^-$ in a mixture comprising a nitrate ($NO_3$), $VCl_3$, HCl, 4,4'-sulfonyldianiline, and N-(1-naphthyl)-ethylenediamine:

For example, a sample suspected of containing $NO_x$ can be reacted with a mixture comprising $VCl_3$, HCl, 4,4'-sulfonyldianiline, and/or N-(1-naphthyl)-ethylenediamine at a temperature of about 70° C.

In one embodiment, a sample suspected of containing $NO_x$ can be reacted in a mixture comprising $VCl_3$, HCl, 4,4'-sulfonyldianiline, and/or N-(1-naphthyl)-ethylenediamine for a period of time sufficient to form a detectable amount of red cationic dye. In a preferred embodiment, a sample suspected of containing $NO_x$ can be reacted in a mixture comprising $VCl_3$, HCl, 4,4'-sulfonyldianiline, and N-(1-naphthyl)-ethylenediamine at 70° C. for about 10 minutes. In this embodiment, the method can be used to visually detect at least about 50 pmoles of $NO_x$ in a 10 microliter sample.

In any of the above embodiments, the method can further comprise cooling the reaction mixture. The reaction mixture can be cooled to room temperature, for example. In any of the above embodiments, the method can further comprise diluting the reaction mixture. The reaction mixture can be diluted with water (e.g., deionized water), for example. In some embodiments, a reaction mixture of about 170 microliters can be diluted with about 830 microliters of deionized water.

In some embodiments, the method further can comprise filtering the mixture. The mixture can be filtered through any filtration media that is suitable to retain the red cationic dye that is a product of the reaction and that does not substantially interfere with the detection or quantitation of the red cationic dye. For example, the mixture can be filtered through a membrane filter (I.C.E. 450, polysulfone membrane, 0.45 μm, part number 66530) available from Pall Gelman (East Hills, N.Y.).

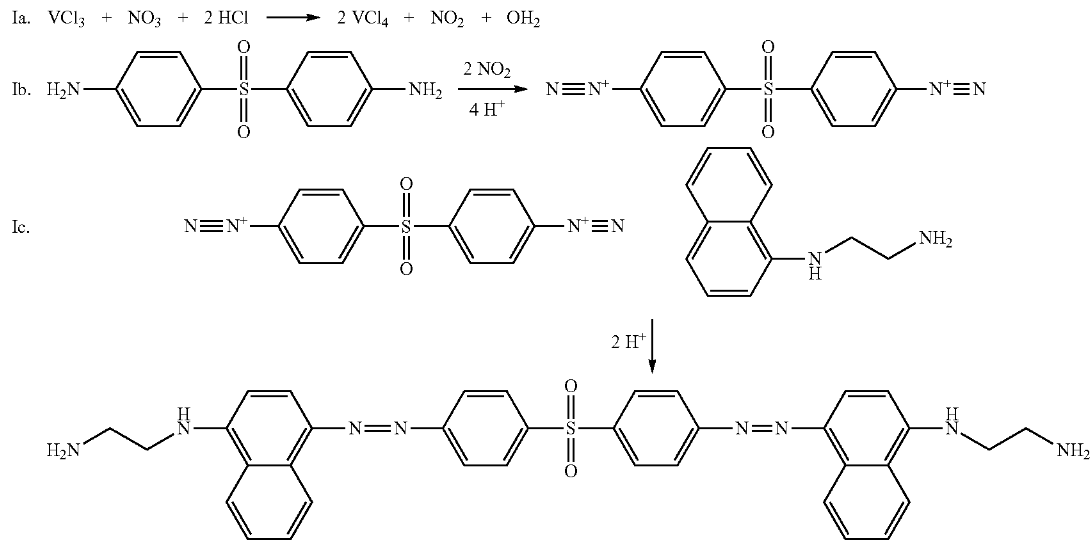

The proposed pathway can include the reduction of $NO_3$ to $NO_2$ in the presence of $VCl_2$ and a strong acid (HCl), as shown in reaction Ia. The proposed pathway further can include the oxidation of p-diaminodiphenyl sulfone in the presence of $NO_2$ and acid, as shown in reaction Ib. The proposed pathway further can include the coupling of two molecules of N-(1-naphthyl)-ethylenediamine to the oxidized form of p-diaminodiphenyl sulfone to form the colored reaction product, as shown in reaction Ic.

Reacting a sample suspected of containing $NO_x$ in a mixture comprising $VCl_3$, HCl, 4,4'-sulfonyldianiline, and/or N-(1-naphthyl)-ethylenediamine can comprise reacting the mixture at an elevated temperature. Elevated temperatures can be used to increase the rate of the reaction, provided the elevated temperature does not substantially decrease the accuracy, sensitivity, and/or reproducibility of the reaction.

FIG. 3a shows a top view of a device 300 for detecting $NO_x$ in a sample. The device comprises an upper layer 310 with a plurality of through-holes 320. The upper layer 310 is preferably constructed from a water-resistant material (e.g., plastic, metal, glass, coated paper). In some embodiments, the upper layer 310 is constructed from a plastic film (e.g., a vinyl tape). In some embodiments, the upper layer 310 may be formed (e.g., by injection molding) with through-holes 320. In some embodiments, the through-holes 320 can be formed (e.g., via a hole punch or perforator) after the upper layer 310 is formed. Positioned beneath the upper layer 310 and coextensive with the cross-sectional area of the through-holes 320 is filter medium 330. The filter medium 330 can be a membrane filter (e.g., a polysulfone membrane filter) with a nominal porosity (e.g., 0.45 μm) suitable to retain the red cationic dye described herein.

Figure 3B:
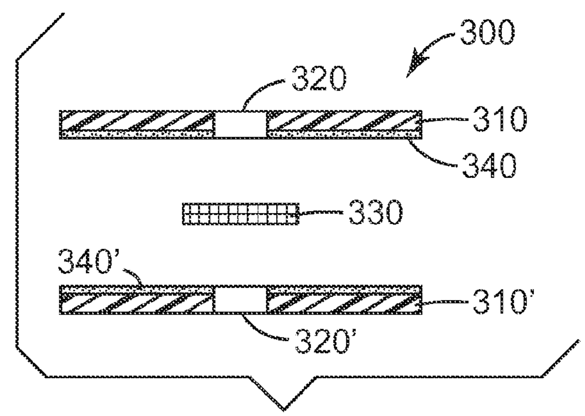
FIG. 3*b* is an exploded side view of the device of FIG. 3*a*.

FIG. 3B shows an exploded cross-sectional side view of the device 300 of FIG. 3B. The device 300 comprises an upper layer 310 and a lower layer 310', each comprising through-holes 320 and 320', respectively. The lower layer 310' can be constructed using processes and materials as described above for the upper layer 310. The upper layer 310 may be constructed from the same material as the lower layer 310'. In some embodiments, the upper layer 310 may be constructed from a different material as the lower layer 310'. Through-holes 320 and 320' are aligned to provide a liquid flow path, in which filter medium 330 is situated, starting at the upper surface and exiting the lower surface of the device 300. The adhesive 340 and 340' secures the filter medium 330 in the liquid flow path and may provide a water-resistant barrier surrounding the exposed filter medium 330. In some embodiments (not shown), the individual flow paths comprising the through-holes can be compartmentalized, such as in a 96-well plate format, for example.

In some embodiments, the red cationic dye retained by the filter can be observed visually. In some embodiments, the red cationic dye retained by the filter can be detected or quantitated using an instrument (e.g., a reflection densitometer RD917, available from GretagMacbeth, Munich, DE). The reflection densitometer can be used with any suitable filter to detect a red-colored compound. In some embodiments, a green filter can be used to detect a red-colored compound.

In any of the above embodiments, the method further can comprise using at least one reference mixture (e.g., one or more "standards") comprising $NO_x$ (e.g., a nitrate salt). In some embodiments, the standard can comprise a threshold standard (e.g., for presence/absence tests). In some embodiments, a plurality of standards can be used to generate a standard curve for quantitative detection. In any of the above embodiments, detecting $NO_x$ in a sample further can comprise comparing the amount of $NO_x$ detected in the sample to the amount of $NO_x$ detected in a standard. In some embodiments, detecting $NO_x$ in a sample further can comprise comparing the amount of $NO_x$ detected in the sample to a standard curve.

Other methods of detecting $NO_x$ in a sample are disclosed in U.S. Patent Application No. 61/231,257, filed on Aug. 4, 2009, which is incorporated herein by reference in its entirety.

Methods of the present disclosure optionally include the detection of one or more analytes other than $NO_x$. In some embodiments, detecting an analyte other than $NO_x$ can comprise detecting total protein. The level of total protein in the specimen can be quantified by any method known in the art which provides adequate sensitivity and reproducibility. The total protein may be detected spectrophotometrically. Spectrophotometric methods include colorimetric methods and fluorometric methods, for example. Detecting total protein colorimetrically can comprise conducting a BCA assay, a Lowry protein assay, a Biuret assay, or a Bradford protein assay, for example. Detecting total protein can further comprise using at least one reference mixture comprising a protein.

In some embodiments, detecting an analyte other than $NO_x$ can comprise detecting a wound analyte (e.g., a protein, a protease, a cytokine, a polynucleotide). Methods for detecting wound analytes (e.g., proteins, enzymes, cytokines, polynucleotides, haptens, and the like) are known in the art and include, for example, chemical detection methods, immunological detection methods, and genetic detection methods. The detection methods may include visual detection or instrument-based detection. Instrument-based detection methods include, for example, spectrophotometric (e.g., colorimetric, fluorometric) detection and mass spectroscopy. In some embodiments, the detection methods may include fractionation of the sample (e.g., purification or partial purification of the analyte by, for example, chromatography).

Kits:

The present disclosure provides kits for detecting $NO_x$ in a wound. Kits may contain certain components that are packaged together for use in methods according to the present disclosure.

In one embodiment, the kit may comprise a sample acquisition device and a reagent for detecting $NO_x$ (e.g., a nitrate compound), wherein the sample acquisition device is substantially free of reactive nitrates. In some embodiments, the sample acquisition device may comprise a wound dressing. In some embodiments, the sample acquisition device may comprise a 3M NEXCARE Soft 'n Flex #672-35 wound dressing. In some embodiments, the kit may further comprise a reagent for detecting a wound analyte other than $NO_x$.

EXAMPLES

Objects and advantages of this invention are further illustrated by the following examples, but the particular materials and amounts thereof recited in these examples, as well as other conditions and details, should not be construed to unduly limit this invention.

All parts, percentages, ratios, etc. in the examples are by weight, unless noted otherwise. Solvents and other reagents used were obtained from Sigma-Aldrich Chemical Company (St. Louis, Mo.), unless otherwise noted.

Estimations of the level of nitrate interference and nonspecific adsorption from various sample acquisition materials were performed. Materials investigated included: 3M NEXCARE "Soft 'n Flex" First Aid Dressing (FAD), available from 3M Company of St. Paul, Minn. (Cat. #672-35); BBL™ Culture swab (220115); and Copan nylon flocked swabs 519CS01 and Copan eSwabs 480C commercially available from COPAN Diagnostics Inc., of Murrieta, Calif.

Example 1

The Copan eSwab was tested to verify its suitability to collect wound fluid samples intended to be analyzed for total protein content. Surrogate samples were prepared using human plasma P9523 available from Sigma-Aldrich Chemical Company of St. Louis, Mo., by diluting the plasma 1:3 and 1:10, in isotonic saline to mimic different wound fluid protein concentrations. A volume of 100 μL of surrogate sample was deposited (spiked) on several eSwabs.

The eSwabs were placed in a microtube containing a small perforated device to hold the swab up but let the fluid flow through during centrifugation to "recover" the sample spiked onto the eSwab. The plastic stem was cut to fit in the tube and all samples were centrifuged at 10,000 rpm for 5 min. The volume recovered from each eSwab appeared to be nearly 100%, since the fluid level was at the 0.1 mL graduated marking on each tube. However, a pellet of swab material was also observed at the bottom of the tube. The fluid was transferred to a clean tube, avoiding not to transfer the small pellet of swab fibers that was observed after centrifugation. It was observed that the eSwab leached a yellow color into the samples.

Both plasma dilutions (1:3 and 1:10, in saline) were run with 6 replicates, 6 different eSwabs. Samples were frozen until further analysis by Pierce BCA (Bicinchoninic Acid) assay, catalogue #23227, available from Thermo Fischer Scientific of Rockford, Ill. The micoplate procedure provided in the kit instructions was followed. A Molecular Devices SPECTRAmaxR2 plate reader was used. Samples were run with appropriate dilutions to fall within the calibration range of the assay, which is 0.025-2.0 mg/ml protein.

Additionally, plasma 1:3, plasma 1:10, saline and HEPES buffer that did not contact an eSwab were analyzed as controls in the BCA assay to provide a baseline. Table 1 below shows the results obtained. Samples that contacted the eSwabs had a higher result than the samples that did not contact any swab, due to some swab component interfering with this assay.

TABLE 1

| eSwab # | Sample Description | Protein concentration (mg/ml) |
|---|---|---|
| — | Plasma 1:3 | 16.66 |
| — | Plasma 1:10 | 5.03 |
| — | Saline (NaCl 0.9%) | Below detection limit |
| — | HEPES buffer 5 mM | Below detection limit |
| 1 | 100 μl plasma 1:3 | 28.82 |
| 2 | 100 μl plasma 1:3 | 27.08 |
| 3 | 100 μl plasma 1:3 | 29.28 |
| 4 | 100 μl plasma 1:3 | 27.32 |
| 5 | 100 μl plasma 1:3 | 26.54 |
| 6 | 100 μl plasma 1:3 | 26.13 |
| 7 | 100 μl plasma 1:10 | 15.08 |
| 8 | 100 μl plasma 1:10 | 15.15 |
| 9 | 100 μl plasma 1:10 | 16.40 |
| 10 | 100 μl plasma 1:10 | 14.70 |
| 11 | 100 μl plasma 1:10 | 14.60 |
| 12 | 100 μl plasma 1:10 | 15.00 |
| 13 | 100 μl Saline (NaCl 0.9%) | 20.45 |
| 14 | 100 μl HEPES buffer 5 mM | 23.75 |

Example 2

An experiment was run to confirm the above results reported in Table 1 for the Copan eSwab. Surrogate samples were prepared using additional concentrations of human plasma (Sigma P9523) to simulate wound fluid. The plasma dilutions prepared were: undiluted, 1:3, 1:10 and 1:50 in saline.

The same procedure for Example A was followed. Again the volume recovered appeared to be nearly 100%. Also, the small pellet of swab material was observed at the bottom of the tube and the eSwab leached a yellow color into the samples.

Plasma dilutions and saline that did not contact a swab were added as controls in the BCA assay to provide a baseline. The table below shows the results obtained and indicates that all samples that contacted swabs had a much higher result than the same original sample that did not contact any swab. This swab led to an overestimation of the protein content of the samples due to some swab component interfering with this assay.

TABLE 2

| eSwab # | Sample Description | Protein concentration (mg/ml) |
|---|---|---|
| — | Plasma, undiluted | 52.00 |
| — | Plasma 1:3 | 16.00 |
| — | Plasma 1:10 | 5.10 |
| — | Plasma 1:50 | 1.04 |
| — | Saline (NaCl 0.9%) | Below detection limit |

TABLE 2-continued

| eSwab # | Sample Description | Protein concentration (mg/ml) |
|---|---|---|
| — | Water | Below detection limit |
| 1 | 100 μL plasma, undiluted | 69.00 |
| 2 | 100 μL plasma, undiluted | 62.00 |
| 3 | 100 μL plasma 1:3 | 28.50 |
| 4 | 100 μL plasma 1:3 | 29.80 |
| 5 | 100 μL plasma 1:10 | 15.10 |
| 6 | 100 μL plasma 1:10 | 16.00 |
| 7 | 100 μL plasma 1:50 | Higher than highest standard (2 mg/ml)* |
| 8 | 100 μL plasma 1:50 | Higher than highest standard (2 mg/ml)* |
| 9 | 100 μL Saline (NaCl 0.9%) | Higher than highest standard (2 mg/ml)* |
| 10 | 100 μL Saline (NaCl 0.9%) | Higher than highest standard (2 mg/ml)* |

*those samples were assayed with the same dilution factor as the corresponding original samples that did not contact any swab.

Example 3

Two different commercially available sample acquisition devices were evaluated to verify their suitability to collect wound fluid samples intended to be analyzed for total protein content, the Copan nylon flocked swab, 519CS01.US and the rayon culture swab, BBL CultureSwab Collection and transport system, BD No. 220115, available from BBL Microbiology Systems Cockeysville, Md.

Surrogate samples were prepared using human plasma (Sigma P9523) to simulate wound fluid in the same manner as Examples A and B, above. Plasma dilutions were: undiluted and 1:10, in saline.

Following the same procedure as with Examples A and B, 100 μL of surrogate sample was deposited (spiked) onto the test swabs and centrifuged for recovery. Similarly to the eSwab, a small pellet of swab material was observed at the bottom of the tube. The fluid was transferred to a clean tube, avoiding transfer of the small pellet of swab fibers that was observed after centrifugation.

A subset of the samples were filtered after centrifugation and before transfer to a clean tube using PALL Life Sciences 4454 Acrodisc syringe filters with 0.2 μm HT TUFFRYN membrane available from Pall Corporation of East Hills, N.Y. This filtration step was to remove any swab component that might have been released during centrifugation.

The Copan nylon flocked swab, 519CS01.US did not absorb the sample readily; the sample beaded up on the swab and it was necessary to pipet up and down and rub the sample into the swab with the pipet tip. This swab also did not leach any visible color into the samples. The swab eluted with water gave a clear water sample with no visible yellow color.

The rayon BBL CultureSwab was very absorbent at first but could barely hold 100 μL. The swab looked very saturated. The filtration step used on a subset of the samples caused a visible loss of fluid.

As with Examples 1 and 2, samples of Example 3 were frozen until further analysis by Pierce BCA (Bicinchoninic Acid) assay, Cat #23227, available from Thermo Fischer Scientific of Rockford, Ill. The micoplate procedure provided in the kit instructions was followed. A Molecular Devices SPECTRAmaxR2 plate reader was used. Samples were run with appropriate dilutions to fall within the calibration range of the assay, which is 0.025-2.0 mg/ml protein. Plasma dilutions (undiluted, 1:10) and saline that did not contact a swab were added as controls in the BCA assay to provide a baseline.

Table 3, below shows the results obtained indicate that the Copan nylon flocked swab, 519CS01.US had minimal, yet variable interference and the rayon BBL CultureSwab had somewhat higher level of interference than the Copan nylon flocked swab.

TABLE 3

| Swab # | Sample Description | Protein concentration (mg/ml) |
|---|---|---|
| — | Plasma, undiluted | 51.00 |
| — | Plasma 1:10 | 4.70 |
| — | Saline | Below detection limit |
| — | Water | Below detection limit |
| 1 | 100 µL plasma, undiluted, Copan 519CS01 | 55.00 |
| 2 | 100 µL plasma 1:10, Copan 519CS01 | 4.50 |
| 3 | 100 µL plasma, undiluted, BBL CultureSwab | 67.00 |
| 4 | 100 µL plasma 1:10, BBL CultureSwab | 5.20 |
| 5 | 100 µL plasma, undiluted, Copan 519CS01, with filtration step | 50.00 |
| 6 | 100 µL plasma 1:10, Copan 519CS01, with filtration step | 4.70 |
| 7 | 100 µL plasma, undiluted, BBL CultureSwab, with filtration step | 65.00 |
| 8 | 100 µL plasma 1:10, BBL CultureSwab, with filtration step | 5.10 |
| 9 | 100 µL water, Copan 519CS01, with filtration step | Below detection limit |
| 10 | 100 µL water, BBL CultureSwab, with filtration step | 0.74 |
| 11 | 100 µL water, Copan 519CS01, no filtration | Below detection limit |
| 12 | 100 µL water, BBL CultureSwab, no filtration | 0.52 |

Example 4

The commercially available Copan nylon flocked swab, 519CS01.US and the BBL CultureSwab BD No. 220115 were further tested to verify their suitability to collect wound fluid samples intended to be analyzed for nitric oxide metabolites content, nitrate ($NO_3^-$) and nitrite ($NO_2^-$).

Surrogate samples were prepared using human plasma (Sigma P9523) to simulate wound fluid. Plasma dilutions (1:3 and 1:10, in saline) were used to mimic different possible wound fluid protein concentrations. Plasma dilution samples were spiked with potassium nitrate solution to give 0, 1 and 20 µM nitrate sample concentrations. Water was also spiked with the same concentrations of nitrate to provide samples of the same nitrate concentrations but without protein content.

A volume of 100 µL of surrogate sample was deposited (spiked) on each swab. The swab was then placed in a microtube containing a cut pipet tip to hold the swab up but let the fluid flow through during centrifugation to recover the sample collected by the swab. The plastic stem was cut to fit in the tube. This was centrifuged at 10,000 rpm for 5 minutes.

Samples were refrigerated overnight for analysis the next day using the Cayman Nitrate/Nitrite fluorometric assay kit (Cat. 780051) using the measurement of nitrate+nitrite procedure. This protocol measured the sum of nitrate and nitrite, termed $NO_x$, by first converting all nitrate into nitrite using nitrate reductase, and then measuring the total nitrite present in the sample. Per kit instructions, all samples containing plasma were filtered prior to the assay. Samples of 100 µL (or 50 µL for the samples having contacted the swab) were used for centrifugation with the MW cut off filters (Microcon Centrifugal Devices from Amicon Bioseparations/Millipore; Ultracel YM-10, Regenerated cellulose, 10 000 MW cut-off, Cat. #42407). They were centrifuged at 14,000 g for 30 min. After this filtration, the samples were all clear. A thin yellow film was visible on the filter units. Filtering 50 µL led to recovery of >20 µL.

A BioTek Synergy 4 plate reader was used. Samples were run with appropriate dilutions to fall within the calibration range of the assay, which is 0.78-50 µM nitrate. Plasma and saline samples as well as water that did not contact a swab were added as controls in the $NO_x$ assay to provide a baseline. Table 4, below shows the results obtained and indicates that both swabs contain high levels of nitrate. Plasma itself also contains significant amounts of nitrate. Nitrate found in wound fluid may in part come from plasma.

TABLE 4

| Tube # | Sample Description | $NO_x$ conc. (µM) |
|---|---|---|
| — | Plasma, undiluted | 62.00 |
| — | Plasma 1:3 | 27.09 |
| — | Plasma 1:3 + 1 µM nitrate | 26.65 |
| — | Plasma 1:3 + 20 µM nitrate | 46.67 |
| — | Plasma 1:10 | 23.95 |
| — | Plasma 1:10 + 1 µM nitrate | 17.29 |
| — | Plasma 1:10 + 20 µM nitrate | 36.60 |
| — | Saline | 2.24 |
| — | Water | 3.71 |
| 1 | Plasma 1:3 (not spiked) on Copan 519CS01 | 118.94 |
| 2 | Plasma 1:10 (not spiked) on Copan 519CS01 | 122.27 |
| 3 | Plasma 1:3 + 1 µM nitrate on Copan 519CS01 | 114.25 |
| 4 | Plasma 1:3 + 20 µM nitrate on Copan 519CS01 | 122.71 |
| 5 | Plasma 1:10 + 1 µM nitrate on Copan 519CS01 | 79.79 |
| 6 | Plasma 1:10 + 20 µM nitrate on Copan 519CS01 | 106.23 |
| 7 | Saline on Copan 519CS01 | 94.20 |
| 8 | Plasma 1:3 (not spiked) on BBL CultureSwab | 125.95 |
| 9 | Plasma 1:10 (not spiked) on BBL CultureSwab | 107.87 |
| 10 | Plasma 1:3 + 1 µM nitrate on BBL CultureSwab | 130.53 |
| 11 | Plasma 1:3 + 20 µM nitrate on BBL CultureSwab | 135.21 |
| 12 | Plasma 1:10 + 1 µM nitrate on BBL CultureSwab | 127.52 |
| 13 | Plasma 1:10 + 20 µM nitrate on BBL CultureSwab | 60.35 |
| 14 | Saline on BBL CultureSwab | 104.81 |

Example 5

A First Aid dressing (FAD), 3M NEXCARE "Soft 'n Flex" box with the 3M Cat. #672-35, commercially available from 3M Company of St. Paul, Minn., was tested to verify its suitability to collect wound fluid samples intended to be analyzed for total protein content and for nitric oxide metabolites, nitrate and nitrite, content.

Surrogate samples were prepared using human plasma (Sigma P9523) to simulate wound fluid. A plasma dilution of 1:10 was used to mimic wound fluid. Plasma dilution samples were spiked with 0, 1, 5, 10, 15, 20 and 25 µM potassium nitrate. In addition, saline was also spiked with the same concentrations of nitrate to provide samples of the same nitrate concentrations but without protein content.

A volume of 150 µL of the various surrogate samples were deposited (spiked) on the several FAD pads. The FAD samples were then placed in a microtube containing a small perforated device to hold the dressing up but let the fluid flow through during centrifugation to recover the sample collected by the dressing pad. The tube was closed and left at room temperature for 30 min (to simulate clinical conditions of sample acquisition). The tube was then frozen at −20° C. overnight. The next day, the tube was thawed and centrifuged at 10,000 rpm for 10 min. The volume recovery was excellent with approximately 140 µL of sample being retrieved.

All samples of EXAMPLE E were then analyzed by Pierce BCA (Bicinchoninic Acid) assay, Cat #23227, using the micoplate procedure provided in the kit instructions. Samples were run with appropriate dilutions to fall within the calibration range of the assay, which is 0.025-2.0 mg/ml protein.

A BioTek Synergy 4 plate reader was used. All samples of EXAMPLE E were also analyzed using the Cayman Nitrate/Nitrite fluorometric assay kit (Cat. 780051) using the measurement of nitrate+nitrite procedure. This protocol measured the sum of nitrate and nitrite, termed $NO_x$, by first converting the entire nitrate into nitrite using nitrate reductase, and then measuring the total nitrite present in the sample. Per kit instructions, all samples containing plasma were filtered prior to the assay. Samples of 50 μL were used for centrifugation with the MW cut off filters (Microcon Centrifugal Devices from Amicon Bioseparations/Millipore; Ultracel YM-10, Regenerated cellulose, 10,000 MW cut-off, Cat. #42407). They were centrifuged at 14,000 g for 30 minutes. Filtering 50 μL of sample led to recovery of >20 μL. A BioTek Synergy 4 plate reader was used. Samples were run with appropriate dilutions to fall within the calibration range of the assay, which is 0.78-50 μM nitrate.

Plasma and saline samples as well as water that did not contact a first aid dressing pad were added as controls in the both assays (total protein and $NO_x$) to provide a baseline. The table below shows the results obtained and indicates that the first aid dressing pad did not interfere with either assay.

TABLE 5

| FAD # | Sample Description | Protein conc. (mg/ml) | $NO_x$ conc. (μM) |
|---|---|---|---|
| — | Plasma 1:10 + 25 μM nitrate | 4.78 | 29.65 |
| — | Plasma 1:10 + 20 μM nitrate | 4.72 | 25.73 |
| — | Plasma 1:10 + 15 μM nitrate | 4.81 | 19.46 |
| — | Plasma 1:10 + 10 μM nitrate | 4.85 | 15.41 |
| — | Plasma 1:10 + 5 μM nitrate | 4.89 | 10.16 |
| — | Plasma 1:10 | 4.96 | 7.42 |
| — | Saline + 25 μM nitrate | Nd/na | 21.38 |
| — | Saline + 20 μM nitrate | Nd/na | 15.87 |
| — | Saline + 15 μM nitrate | Nd/na | 11.75 |
| — | Saline + 10 μM nitrate | Nd/na | 5.17 |
| — | Saline + 5 μM nitrate | Nd/na | −0.34 |
| — | Saline + 1 μM nitrate | Nd/na | −7.77 |
| — | Saline | −0.03 | −2.91 |
| — | water | −0.03 | −2.61 |
| 1 | Plasma 1:10 + 25 μM nitrate | 4.64 | 34.74 |
| 2 | Plasma 1:10 + 20 μM nitrate | 4.79 | 25.69 |
| 3 | Plasma 1:10 + 15 μM nitrate | 4.35 | 24.03 |
| 4 | Plasma 1:10 + 10 μM nitrate | 4.88 | 15.62 |
| 5 | Plasma 1:10 + 5 μM nitrate | 4.65 | 12.30 |
| 6 | Plasma 1:10 | 4.81 | 9.50 |
| 8 | Saline + 25 μM nitrate | Nd/na | 22.96 |
| 9 | Saline + 20 μM nitrate | Nd/na | 18.79 |
| 10 | Saline + 15 μM nitrate | Nd/na | 12.55 |
| 11 | Saline + 10 μM nitrate | Nd/na | 9.44 |
| 12 | Saline + 5 μM nitrate | Nd/na | 1.37 |
| 13 | Saline + 1 μM nitrate | Nd/na | −9.78 |
| 14 | Saline | −0.03 | −2.18 |
| 15 | water | −0.03 | −3.84 |

Nd/na: Not done/not applicable.

The spiked saline samples were not analyzed in the BCA assay since they are not expected to contain any proteins and would all be zero.

Note that the nitrate contents is irrelevant in the total protein assay (BCA); the same samples prepared for the $NO_x$ assay were used to provide several replicates of plasma samples for the BCA assay.

Example 6

Matrix metalloproteinase MMP-9 activity was assayed using the R&D Systems Fluorokine E Human Active MMP-9 Assay F9M00 from samples spiked onto the 3M NEXCARE Soft'n Flex bandage FAD.

150 μL of the 32 ng/mL stock MMP-9 was spiked onto a ¾"×3" dressing. The adhesive tabs were cut off. The dressing was rolled so that the pad was inside the FAD. The FAD was then placed into a microcentrifuge tube containing a frit to keep it suspended above the bottom of the tube. This is allowed to sit at room temperature for 30 minutes to simulate clinical conditions of sample acquisition. After 30 minutes the tubes were spun for 8 minutes at 10RCF. Visual inspection of the tube graduations indicate nearly 100% fluid recovery. Next an amount of 110 μL of the centrifugate was combined with 110 μL of RD5-24 assay buffer for a presumed concentration of 16 ng/mL MMP-9. A standard curve of concentrations of 0.5, 1, 2, 4, 8 and 16 ng/mL MMP-9 was prepared from the 32 ng/mL stock solution. The assay was run as per the Fluorokine E assay protocol for serum/plasma samples and analyzed on a BioTek Synergy4 fluorescent plate reader. An amount of 50 μL of RD1N assay buffer was added to each well. Next 200 μL of standards and samples were added to the wells, including the spiked FAD and water blank. The plate was shaken at room temperature for 2.5 hours at 200 RMP in Shell Incubator and the plate was washed as per protocol. Next 200 μL of APMA was added, incubated for 2 hours at 37° C. in the dark. The plate washed as per protocol again and 200 μL of substrate added, incubated for 18 hours at 37° C. in the dark. Finally the plate was read at EM=320 nm, EX=405 nm.

TABLE 6

| | ng/mL | Average RFU |
|---|---|---|
| MMP-9 Standard 16 | 16 | 1823 |
| MMP-9 Standard 8 | 8 | 1304 |
| MMP-9 Standard 4 | 4 | 863 |
| MMP-9 Standard 2 | 2 | 487 |
| MMP-9 Standard 1 | 1 | 264 |
| MMP-9 Standard 0.5 | 0.5 | 145 |
| Sample FAD Spike 1 | 16 | 2005 |
| Sample FAD Spike 2 | 16 | 1981 |
| Sample FAD Spike 3 | 16 | 2027 |

Example 7

A set of nitrate standards were prepared from a stock solution of a potassium nitrate salt in water. The stock solution was further diluted in water to the following concentrations: 0, 5, 10, 15, 20, 25 and 30 μM, respectively. The diluted solutions were the "samples" used in the assay described below.

Reagent 1 was prepared by mixing 0.1 g of each of Components A and B with 49.8 g water. Component A consisted of a 1% (w/v) solution of dapsone (4,4'-sulfonyldianiline, Aldrich catalog no. A7480-7, Sigma-Aldrich, St. Louis, Mo.) in 1N HCl. Component B consisted of 0.05% (w/v) NEDD (N-(1-naphthyl)ethylene-diamine dihydrochloride, Eastman catalog no. 4835, Eastman Chemical Company, Kingsport, Tenn.) in water. Reagent 2 consisted of vanadium chloride ($VCl_3$) 0.1% (w/v) in 20% HCl.

Ten microliters of each sample was added to a microcentrifuge tube, where it was combined and mixed with 140 μl Reagent 1 and 20 μl Reagent 2. The tube was incubated at 70° C. for 10 min and cooled to room temperature. 830 μl of deionized water was added to the tube and the resulting mixture was filtered as described below.

Strips of white tape were perforated with 2.0 mm diameter holes. A laminate was formed by inserting membrane filter disks (¼ inch (6.35 mm) diameter, die-cut from Pall Gelman Lab I.C.E. 450, polysulfone membrane 0.45 μm, part number 66530) between two layers of tape such that the holes in the top layer of tape were superimposed over the holes in the bottom layer of tape with the filter membrane material located in the opening created by the superimposed holes. The laminate was placed over a 96-well plate configured for vacuum filtration such that a sample placed into the well of the plate could be drawn through the filter in the 2 mm opening. The membrane filter retained a red cationic dye in the samples containing nitrate.

Figure 4:
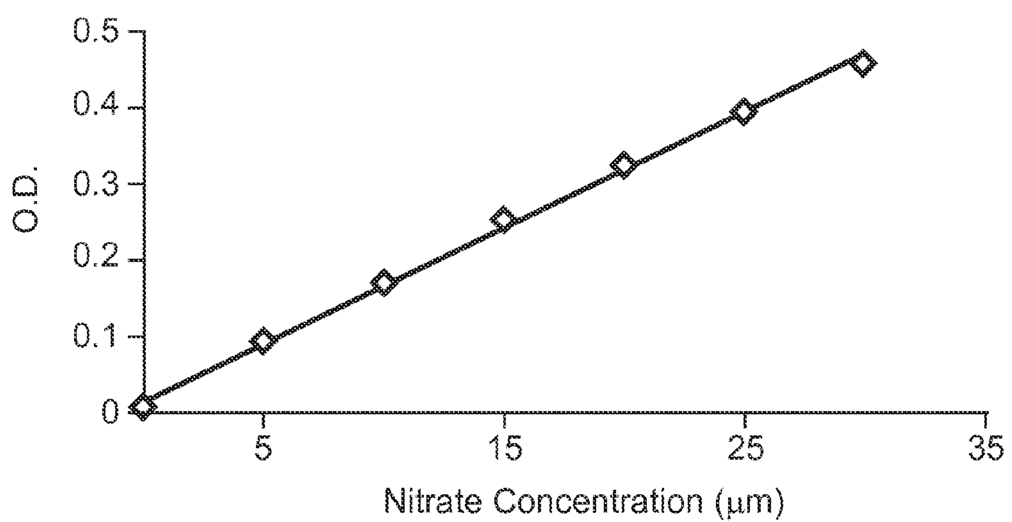
FIG. 4 is a graph of data from a reflective densitometer.

The intensity (optical density) of the color in each well was measured with a reflection densitometer (MacBeth RD917) using the green filter. A plot of the relationship between the concentration of nitrate in the sample and the optical density of the color retained by the filter is shown in FIG. 4. The linearity of the reaction can be observed in this standard curve shown in FIG. 4.

Example 8

The detection system described in Example 7 was used to test the nitrate levels of various commercially-available absorbent materials. The materials included several grades of filter paper that are purported to contain extremely low levels of nitrates.

A standard containing 10 μM was prepared and tested as described in Example 7. Samples of absorbent materials (1 cm×1 cm squares of four grades of filter paper and one 3M NEXCARE Soft 'n Flex #672-35 first aid dressing) were placed in a tube and was wetted with 0.05 mL of the nitrate-free assay buffer (CaymanNitrate/Nitrite fluorometric assay kit, catalog no. 780051, Cayman Chemical Company) and was allowed to stand at room temperature for about 30 minutes. The buffer was extracted from the absorbent article by centrifugation at 10,000 rpm in a microcentrifuge, and 10 microliters of the extracted buffer was tested according to the procedure described in Example 7. The color of the membrane filters from the nitrate test from each absorbent material was compared to the color of the membrane filter of the 10 mM nitrate standard. Any test showing a darker shade of red than the standard was recorded as "yes". The results are shown in Table 7. The data indicate that all of the filter papers that were tested contained endogenous levels of nitrate that are high enough to interfere with the detection of physiological levels of $NO_x$ using the method described in Example 7. In contrast, the first aid dressing did not contain endogenous levels of nitrate that are high enough to interfere with the detection of physiological levels of $NO_x$ using the method described in Example 7.

TABLE 7

| Absorbent Article | Type | ≥10 μM |
|---|---|---|
| Filter | WHATMAN #5 | Yes |
| Filter | WHATMAN #40 | Yes |
| Filter | WHATMAN #50 | Yes |
| Filter | WHATMAN #54 | Yes |
| First Aid Dressing | 3M NEXCARE #672-35 | No |

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method comprising:

providing a sample acquisition device comprising an absorbent pad that comprises less than 31 ng of reactive nitrates per $cm^2$;

contacting the sample acquisition device with a wound site for about 24 hours or less;

extracting a portion of the exudate from the absorbent pad of the sample acquisition device; and detecting endogenous NOx in the extracted portion.

2. The method of claim 1, further comprising detecting in at least one extracted portion at least one analyte in addition to endogenous $NO_x$.

3. The method of claim 2, wherein detecting in the extracted portion at least one analyte in addition to endogenous $NO_x$ comprises detecting total protein.

4. The method of claim 3, wherein detecting total protein comprises detecting protein colorimetrically.

5. The method of claim 2, wherein detecting in the extracted portion at least one analyte in addition to endogenous $NO_x$ comprises detecting a protease.

6. The method of claim 2, wherein detecting at least one analyte in addition to endogenous NOx comprises detecting an analyte from the group consisting of: detecting total protein, a protein or a fragment thereof, a protease, a polynucleotide, a cytokine, a growth factor, a microorganism or an analyte therefrom, or a combination of any two or more of the foregoing analytes.

7. The method of claim 2, wherein detecting in the extracted portion at least one analyte in addition to endogenous NOx comprises detecting total protein and matrix metalloproteinase MMP-9.

8. The method of claim 1, wherein detecting endogenous $NO_x$ comprises detecting $NO_x$ by spectrometry.

9. The method of claim 8, wherein detecting $NO_x$ by spectrometry comprises detecting $NO_x$ colorimetrically.

10. The method of claim 8, wherein detecting $NO_x$ by spectrometry comprises detecting $NO_x$ fluorometrically.

11. The method of claim 1, wherein extracting the exudate comprises centrifuging the sample acquisition device.

12. The method of claim 1, further comprising the step of measuring the pH of the wound.

13. The method of claim 1, further comprising cleansing the wound.

14. The method of claim 1, wherein contacting the sample acquisition device with a wound site for a period of time comprises manually pressing the device against the wound site.

15. The method of claim 1, wherein contacting the sample acquisition device with a wound comprises contacting the sample acquisition device with a wound site for less than 30 minutes.

16. The method of claim 15, wherein contacting the sample acquisition device with a wound comprises contacting the sample acquisition device with a wound site for less than 1 minute.

17. The method of claim 1, wherein, after the sample acquisition device is contacted with the wound site, the sample acquisition device is frozen.

18. A method comprising:

providing at least two sample acquisition devices, each sample acquisition device comprising an absorbent pad that comprises less than 31 ng of reactive nitrates per $cm^2$;

contacting a first sample acquisition device with a wound site for about 24 hours or less;

cleansing the wound site;

contacting a second sample acquisition device with the wound site for about 24 hours or less;

extracting a portion of the exudate from the absorbent pad of each of the first and second sample acquisition devices; and detecting endogenous NOx in the extracted portion from each sample acquisition device.

* * * * *

UNITED STATES PATENT AND TRADEMARK OFFICE

CERTIFICATE OF CORRECTION

PATENT NO. : 8,703,101 B2
APPLICATION NO. : 13/388360
DATED : April 22, 2014
INVENTOR(S) : Bernatchez et al.

It is certified that error appears in the above-identified patent and that said Letters Patent is hereby corrected as shown below:

In the Specification

Column 1
Line 56, "that that" should read --that--.

Column 3
Line 52, "disclosure" should read --disclosure.--.

Column 4
Line 6, "2A-11A)" should read --2A-11A).--.

Column 6
Line 35, "FIG. 1 a." should read --FIG. 1a.--.

Column 9
Line 49, "nitrate. nitrite." should read --nitrate, nitrite,--.

Column 10
Line 19, "diaminonaphalene" should read --diaminonaphthalene--.

Column 15
Line 5, "micoplate" should read --microplate--.

Column 16
Line 60, "micoplate" should read --microplate--.

Column 19
Line 1, "micoplate" should read --microplate--.

Signed and Sealed this
Fifth Day of May, 2015

Michelle K. Lee
*Director of the United States Patent and Trademark Office*

Column 20
Line 16, “Synergy4” should read --Synergy 4--.